US010357613B2

United States Patent
Jugl et al.

(10) Patent No.: US 10,357,613 B2
(45) Date of Patent: Jul. 23, 2019

(54) ASSEMBLY FOR A DRUG DELIVERY DEVICE

(71) Applicant: Sanofi-Aventis Deutschland GMBH, Frankfurt am Main (DE)

(72) Inventors: Michael Jugl, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 259 days.

(21) Appl. No.: 14/914,760

(22) PCT Filed: Aug. 15, 2014

(86) PCT No.: PCT/EP2014/067473
§ 371 (c)(1),
(2) Date: Feb. 26, 2016

(87) PCT Pub. No.: WO2015/028319
PCT Pub. Date: Mar. 5, 2015

(65) Prior Publication Data
US 2016/0206824 A1  Jul. 21, 2016

(30) Foreign Application Priority Data
Aug. 28, 2013 (EP) .................................... 13181946

(51) Int. Cl.
*A61M 5/315* (2006.01)
(52) U.S. Cl.
CPC .... *A61M 5/31541* (2013.01); *A61M 5/31555* (2013.01); *A61M 5/31585* (2013.01)

(58) Field of Classification Search
CPC .......... A61M 5/31541; A61M 5/31555; A61M 5/31585; A61M 5/24; A61M 5/31551;
(Continued)

(56) References Cited

U.S. PATENT DOCUMENTS

| 3,494,358 A * | 2/1970 | Duesterheft | A61M 5/20 604/137 |
| 2005/0197650 A1* | 9/2005 | Sugimoto | A61M 5/20 604/890.1 |

(Continued)

FOREIGN PATENT DOCUMENTS

| CN | 102186517 | 9/2011 |
| CN | 102281909 | 12/2011 |

(Continued)

OTHER PUBLICATIONS

International Search Report and Written Opinion in International Application No. PCT/EP2014/067473, dated Apr. 2, 2015, 10 pages.

(Continued)

*Primary Examiner* — Laura A Bouchelle
*Assistant Examiner* — Dung T Ulsh
(74) *Attorney, Agent, or Firm* — Fish & Richardson P.C.

(57) ABSTRACT

An assembly for a drug delivery device includes an actuator configured to perform a setting movement in order to set a dose of medication and to perform a dispense movement in order to dispense a dose of medication. The assembly further includes a stop mechanism which is configured to allow a setting movement of the actuator after a maximum amount of medication has been delivered and to inhibit a dispense movement of the actuator after a setting movement when a maximum amount of a medication has been delivered.

17 Claims, 3 Drawing Sheets

(58) Field of Classification Search
CPC .......... A61M 5/31593; A61M 5/31451; A61M 5/31543; A61M 5/3157; A61M 5/3158; A61M 5/31533; A61M 5/31583; A61M 5/31568

See application file for complete search history.

(56) References Cited

U.S. PATENT DOCUMENTS

| | | | |
|---|---|---|---|
| 2009/0240195 A1 | 9/2009 | Schrul et al. | |
| 2010/0094205 A1 | 4/2010 | Boyd et al. | |
| 2010/0152671 A1* | 6/2010 | Raab | A61M 5/31555 604/207 |
| 2010/0152672 A1 | 6/2010 | Raab | |
| 2011/0172640 A1* | 7/2011 | Cronenberg | A61M 5/31555 604/506 |
| 2012/0265151 A1 | 10/2012 | Nzike et al. | |
| 2012/0283658 A1 | 11/2012 | Plumptre et al. | |
| 2014/0046268 A1* | 2/2014 | Quinn | A61M 5/31541 604/209 |
| 2015/0080811 A1* | 3/2015 | Wieselblad | A61M 5/3155 604/207 |
| 2015/0174335 A1* | 6/2015 | Roervig | A61M 5/20 604/198 |
| 2015/0343157 A1* | 12/2015 | Basile | A61M 5/31511 604/506 |
| 2015/0367078 A1* | 12/2015 | Pedersen | A61M 5/31541 604/208 |
| 2016/0317745 A1* | 11/2016 | Kjeldsen | A61M 5/20 |
| 2017/0182255 A1* | 6/2017 | Strehl | A61M 5/31536 |

FOREIGN PATENT DOCUMENTS

| | | |
|---|---|---|
| JP | 2006-204918 | 8/2006 |
| JP | 2010-500136 | 1/2010 |
| JP | 2010-509956 | 4/2010 |
| JP | 2012-511359 | 5/2012 |
| WO | WO 2006/079900 | 8/2006 |
| WO | WO2008/058665 | 5/2008 |
| WO | WO 2010/033770 | 3/2010 |
| WO | WO 2010/066796 | 6/2010 |
| WO | WO 2010/066797 * | 6/2010 |
| WO | WO2011/069935 | 6/2011 |

OTHER PUBLICATIONS

International Preliminary Report on Patentability in International Application No. PCT/EP2014/067473, dated Mar. 1, 2016, 7 pages.
Rote Liste, "50. Hypophysen-, Hypothalamushormone, andere regulatorische Peptide u. ihre Hemmstoffe," Chapter 50, ed. 2008, 20 pages.

* cited by examiner

ASSEMBLY FOR A DRUG DELIVERY DEVICE

CROSS-REFERENCE TO RELATED APPLICATIONS

This application is a U.S. national stage application under 35 USC § 371 of International Application No. PCT/EP2014/067473, filed on Aug. 15, 2014, which claims priority to European Patent Application No. 13181946.8, filed on Aug. 28, 2013, the entire contents of which are incorporated herein by reference.

TECHNICAL FIELD

The present disclosure relates to an assembly for a drug delivery device. The assembly comprises a stop mechanism.

BACKGROUND

A drug delivery device and an assembly for a drug delivery device are described for example in document WO 2008/058665 A1.

SUMMARY

Certain embodiments of the present invention provide assemblies for drug delivery devices having improved properties.

An assembly for a drug delivery device is provided, the assembly comprising an actuator which is configured to perform a setting movement in order to set a dose of medication, and which is configured to perform a dispense movement in order to dispense a dose of medication. The assembly further comprises a stop mechanism which is configured to allow a setting movement of the actuator after a maximum amount of medication has been delivered and to inhibit a dispense movement of the actuator after a setting movement when a maximum amount of medication has been delivered. The maximum amount of medication may be for example the amount of medication available in a cartridge.

The advantage of a stop mechanism which is configured to allow a setting movement of the actuator after a maximum amount of medication has been delivered and to inhibit an dispense movement of the actuator after a setting movement when a maximum amount of a medication has been delivered is that the stop mechanism may permanently lock the assembly after a last setting movement. When the assembly is locked, a movement of any component of the assembly may be inhibited. A further advantage of the stop mechanism is that the assembly may be locked in a state after a setting movement. For example, the actuator may protrude from the drug delivery device in the locked state. Thereby, a user may recognize at first sight that the device is empty.

The setting movement of the actuator may be a translational movement in a proximal direction. In particular, the actuator may be moved in a proximal direction by a user. In particular, the actuator may be moved in a proximal direction until it reaches a mechanical stop. The dispense movement of the actuator may be a movement in a distal direction, for example a purely axial movement. In particular, the actuator may be pushed in a distal direction by a user in order to dispense a dose. The actuator may be configured as a button.

The term "proximal direction" may describe a direction away from a dispensing end of the device. The term "distal direction" may describe a direction towards a dispensing end of the device.

According to one embodiment, the assembly may comprise a main housing part, wherein the actuator may be configured to be depressed towards the main housing part in order to dispense a dose of medication. In particular, the actuator may be depressed towards the main housing part until it abuts a mechanical stop at the end of a dispense operation. Such a depression of the actuator towards the main housing part may be inhibited after a maximum amount of medication has been delivered. In particular, after a maximum amount of medication has been delivered, a depression of the actuator towards the main housing part may be inhibited before the actuator abuts the mechanical stop. In particular, a depression of the actuator may be inhibited by means of the stop mechanism after a maximum amount of medication has been delivered. In order to set a dose, the actuator may be moved in a proximal direction, such that the actuator protrudes from the main housing part. The actuator may be axially moveable and rotationally fixed with respect to the main housing part.

According to one embodiment, the actuator may be configured to perform one last setting movement after a maximum amount of medication has been delivered. After the last setting movement, a dispense movement of the actuator may be inhibited. In particular, the actuator may permanently protrude from the main housing part after the last setting movement. Thereby, an indication may be given to a user that a last dose has been dispensed.

According to one embodiment, the stop mechanism may comprise a first stop element and a second stop element, wherein the first stop element and the second stop element may be configured to interact with each other. When the first stop element and the second stop element interact with each other, a dispensing of a dose may be inhibited. The first stop element and the second stop element may be configured to interact with each other after a last setting movement. In particular, the first stop element and the second stop element may interact with each other after a last setting movement when a user tries to operate the actuator.

According to one embodiment, the first stop element and the second stop element may abut each other after a last dose of medication has been delivered. In particular, the first stop element and the second stop element may abut each other such that they may be moved along each other in an axial direction. Yet, they may not rotate with respect to each other after a last dose of medication has been delivered. In a further embodiment the first stop element and the second stop element may abut each other such that they may not be moved along each other in an axial direction.

According to one embodiment, the second stop element may be configured to be moved along the first stop element in a proximal direction during the last setting movement. A movement of the second stop element along the first stop element in a distal direction may be inhibited by the stop mechanism after the last setting movement.

According to one embodiment, the first stop element may be configured as a longitudinal protrusion. According to a further embodiment, the first stop element may be configured as a spring element, for example a resilient arm. The spring element may be configured to be deflected in a radial direction. In particular, the spring element may be configured to be deflected in a radial inward direction during a last setting movement of the actuator. The spring element may be deflected when the second stop element is moved along the first stop element. At the end of the last setting movement, the first stop element, respectively the spring element may relax into its undeflected position. At its proximal end, first stop element, respectively the spring element may comprise a cut-out. The first stop element may extend along a longitudinal axis of the assembly. During the setting of a dose, the first stop element may be axially and rotationally secured with respect to the main housing part. During the dispensing of a dose, the first stop element may move, in particular carry out a rotational and/or translational movement.

According to one embodiment, the assembly may comprise a piston rod, wherein the first stop element may be attached to the piston rod. The first stop element may be an integral part of the piston rod or may be fixedly coupled to the piston rod. In particular, the first stop element may be integrally moulded with the piston rod. In particular, the first stop element may be configured as a protrusion on the piston rod. In an alternative embodiment, the first stop element may be configured as a spring element, in particular a resilient arm, on the piston rod. At a proximal end of the spring element, the piston rod may comprise a piston rod hole. The piston rod may be configured as a lead screw. During the dispensing of a dose, the piston rod may perform a combined axial and rotational movement in a distal direction. During the setting of a dose, the piston rod may be axially and rotationally secured with respect to the main housing part. Since the first stop element is fixedly coupled to the piston rod, the movement of the first stop element may correspond to the movement of the piston rod.

According to one embodiment, the stop mechanism is configured to inhibit a movement of the piston rod in a distal direction after a maximum amount of medication has been delivered. In particular, by means of the stop mechanism, a rotation of the piston rod may be inhibited. Thereby, also an axial movement of the piston rod in a distal direction may be inhibited, since the piston rod may only perform a combined axial and rotational movement. In particular, the assembly may be locked by means of the stop mechanism, such that no further dispense operation is possible.

The second stop element may be configured as a protrusion, for example a protrusion extending in a radial inward direction of the assembly. The second stop element may be coupled to the actuator, such that the movement of the second stop element may correspond to the movement of the actuator.

According to one embodiment, the assembly may comprise a drive member which is configured to drive the piston rod. The second stop element may be attached to the drive member. In particular, the second stop element may be configured as a protrusion on the drive member. For example, the second stop element may be integrally moulded with the drive member. The drive member may be configured as a drive sleeve. The drive member may be engaged with the piston rod, for example by means of a thread. The drive member may be arranged concentrically around the piston rod. The drive member may be fixedly coupled to the actuator. For example, the drive member and the actuator may be manufactured as one piece. In particular, a movement of the actuator may cause a movement of the drive member. Since the drive member and the actuator may be fixedly coupled to each other, the movement of the drive member may correspond to the movement of the actuator.

According to one embodiment, the drive member may be configured to be moved in a proximal direction with respect to the piston rod during the setting movement of the actuator. In particular, the drive member may be configured to perform an axial, non-rotational movement during the setting of a dose. In particular, the drive member may be rotationally fixed with respect to the main housing part during a setting movement and during the dispensing of a dose.

According to one embodiment, the drive member is configured to be moved in a distal direction during the dispensing of a dose, wherein the stop mechanism is configured to inhibit a movement of the drive member in a distal direction after the last setting movement.

When the drive member is moved in a distal direction during the dispensing of a dose, a force may be exerted on the piston rod, which acts in a distal direction. Thereby, the piston rod may be caused to perform a combined axial and rotational movement in a distal direction. In particular, the piston rod may be configured to rotate with respect to the drive member during the dispensing of a dose.

The stop mechanism may be configured to inhibit a relative rotation between the drive member and the piston rod. When a last dose of medication has been delivered, the first stop element of the piston rod and the second stop element of the drive member may abut each other such that the piston rod and the drive member are rotationally fixed with respect to each other. In particular, the stop mechanism may inhibit a rotation of the piston rod in a dispensing direction. The second stop element of the drive member may move in a proximal direction along the first stop element of the piston rod such that a last setting movement may be enabled. According to one embodiment, the second stop element engages with the cut-out of the first stop element. In particular, the first stop element snaps over the second stop element at the end of the last setting movement. When a relative rotation of the drive member and the piston rod is inhibited, a dispense operation is inhibited after the last setting movement. In particular, a distal movement of the drive member and the piston rod is inhibited. Thereby, the assembly is locked.

Furthermore, a drug delivery device is provided, the drug delivery device comprising an assembly which is configured as previously described. In particular, the drug delivery device may comprise a stop mechanism, which is configured to allow a setting movement of the actuator after a last dose of medication has been delivered and to inhibit an actuation of the actuator after a setting movement when a maximum amount of a medication has been delivered.

The drug delivery device may be an injection device. The drug delivery device may be a pen-type device. The drug delivery device may be a fixed dose device such that the amount of medication which is delivered during one dispense operation is predetermined. In particular, a user may not be enabled to vary the size of the dose. The drug delivery device may be configured for multiple dose applications. The medication may be delivered to a user by means of a needle. The device may be delivered to a user in a fully assembled condition ready for use. The drug delivery device may be a disposable device. The term "disposable" means that the drug delivery device cannot be reused after an available amount of medication has been delivered from the drug delivery device. The drug delivery device may be configured to deliver a liquid medication. The medication may be, for example, insulin.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(0)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(02)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further features, refinements and expediencies become apparent from the following description of the exemplary embodiments in connection with the figures.

DETAILED DESCRIPTION

Figure 1:
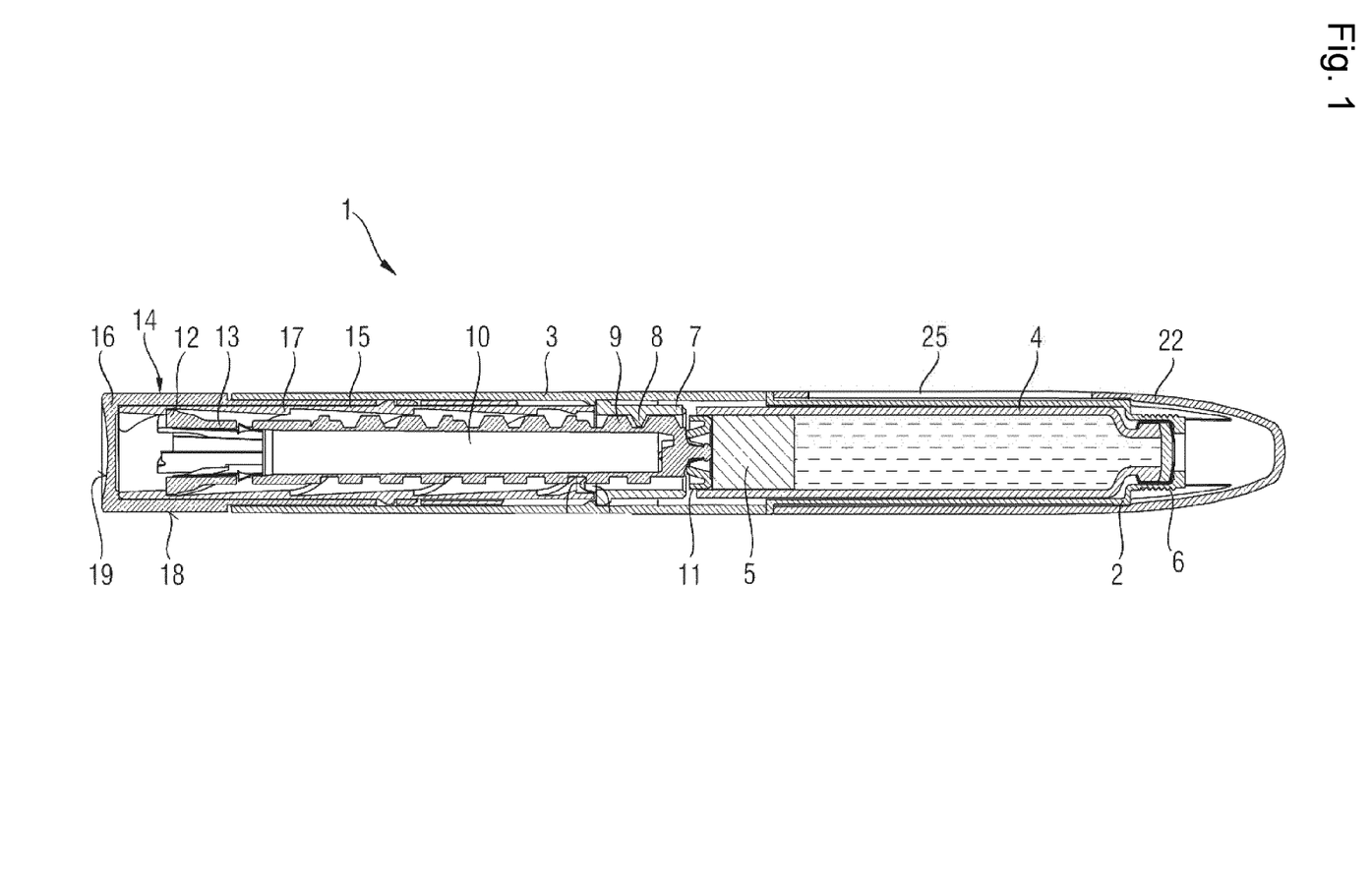
FIG. 1 shows a sectional view of a drug delivery device.

FIG. 1 shows a sectional view of a drug delivery device 1. The drug delivery device 1 comprises a cartridge retaining part 2, and a main housing part 3. The proximal end of the cartridge retaining part 2 and the distal end of the main housing 3 are secured together by any suitable means known to the person skilled in the art. In the illustrated embodiment, the cartridge retaining part 2 is secured within the distal end of the main housing part 3.

A cartridge 4 from which a number of doses of a medicinal product may be dispensed is provided in the cartridge retaining part 2. A piston 5 is retained in the proximal end of the cartridge 4.

A removable cap 22 is releasably retained over the distal end of the cartridge retaining part 2. The removable cap 22 is optionally provided with one or more window apertures through which the position of the piston 5 within the cartridge 4 can be viewed.

The distal end of the cartridge retaining part 2 in the illustrated embodiment, is provided with a distal threaded region 6 designed for the attachment of a suitable needle assembly (not shown) to enable medicament to be dispensed from the cartridge 4.

In the illustrated embodiment, the main housing part 3 is provided with an internal housing 7. The internal housing 7 is secured against rotational and/or axial movement with respect to the main housing part 3. The internal housing 7 is provided with a threaded circular opening 8 extending through the distal end of the internal housing 7. In the illustrated embodiment the threaded circular opening 8 comprises a series of part threads rather than a complete thread. Alternatively, the internal housing 7 may be formed integrally with the main housing part 3. Additionally, the internal housing 7 is provided with a plurality of guide slots and pawl means.

A first thread 9 is formed at the distal end of the piston rod 10. The piston rod 10 is of generally circular cross-section. The first thread 9 of the piston rod 10 extends through and is threadedly engaged with the threaded circular opening 8 of the internal housing 7. A pressure foot 11 is located at the distal end of the piston rod 10. The pressure foot 11 is disposed to abut the proximal face of the piston 5. A second thread 12 is formed at the proximal end of the piston rod 10. In the illustrated embodiment the second thread 12 comprises a series of part threads, rather than a complete thread, formed on flexible arms 13 of the piston rod 10.

The first thread 9 and the second thread 12 are oppositely disposed.

In the illustrated embodiment the first thread 9 is provided with a plurality of features (not shown) that cooperate with the part threads of the threaded circular opening 8 to prevent movement of the piston rod 10 in the proximal direction during setting of the dose.

A drive member 14 extends about the piston rod 10. The drive member 14 is configured as a drive sleeve. The drive member 14 comprises a threaded part 15 of a generally cylindrical cross-section. An actuator 16 is located at a proximal end of the drive member 14. The threaded part 15 and the actuator 16 are secured to each other to prevent rotational and/or axial movement there between. Alternatively, the drive member 14 may be a unitary component consisting of an integrated threaded part 15 and actuator 16.

In the illustrated embodiment, the threaded part 15 is provided with a longitudinally extending helical thread 17 formed on the internal cylindrical surface. The flank of the proximal side of the helical thread 17 is designed to maintain contact with the second thread 12 of the piston rod 10 when dispensing a dose, whilst the flank of the distal side of the helical thread 17 is designed to allow the second thread 12 of the piston rod 10 to disengage when setting a dose. In this way the helical thread 17 of the threaded part 15 is releasably engaged with the second thread 12 of the piston rod 10.

The drive member 14 has a plurality of features formed on the external surface designed to move axially within the guide slots of the internal housing 7. These guide slots define the extent of permissible axial movement of the drive member 14 with respect to the housing part 3. In the illustrated embodiment the guide slots also prevent rotational movement of the drive member 14 relative to the main housing part 3.

The actuator 16 has a plurality of grip surfaces 18 and a dispensing face 19.

To increase intuitiveness of the operation of the device, the main housing part 3 may be provided with a window aperture through which graphical status indicators, provided on the drive member 14, can be viewed.

Operation of the drug delivery device in accordance with certain embodiments of the present invention will now be described.

To set a dose a user grips the grip surfaces 18 of the drive member 14. The user then pulls the drive member 14 in a proximal direction away from the main housing part 3.

The piston rod 10 is prevented from moving proximally by the part threads of the threaded circular opening 8 of the internal housing 7 interacting with thread features on the first thread 9 of the piston rod 10 or by any other suitable means. As the drive member 14 travels in the proximal direction relative to the piston rod 10, the second thread 12 of the piston rod 10 is displaced radially inwards by the flank of the distal side of helical thread 17 of the drive member 14.

The proximal travel of the drive member 14 is limited by the guide slots (not shown) of the internal housing 7 a distance corresponding to essentially one thread pitch of the helical thread 17 of the drive member 14. At the end of the travel of the drive member 14, the second thread 12 of the piston rod 10 engages with the helical thread 17 under the action of the flexible arms 13 of the piston rod 10. By this action the drive member 14 is displaced a distance essentially equal to one pitch of the helical thread 17 of the drive member 14 in the proximal direction relative to the piston rod 10. The action of the second thread 12 positively engaging the helical thread 17 of the drive member 14 under a force provided by the flexible arms 13 creates an audible and tactile feedback to the user to indicate that the dose has been set. Additionally, visual feedback regarding dose setting may be indicated by an optional graphical status indicator, provided on the drive member 14, which can be viewed through an optional window aperture in the main housing part 3.

When the dose has been set, the user may then dispense this dose by depressing the dispensing face 19 of the actuator 16. By this action the drive member 14 is moved axially in the distal direction relative to the main housing part 3. As the second thread 12 of the piston rod 10 is positively engaged with the helical thread 17 of the drive member 14 the piston rod 10 is caused to rotate with respect to the internal housing 7 by the axial movement of the drive member 14 in the distal direction. As the piston rod 10 rotates, the first thread 9 of the piston rod 10 rotates within the threaded circular opening 8 of the internal housing 7 causing the piston rod 10 to move axially in the distal direction with respect to the internal housing 7.

The distal axial movement of the piston rod 10 causes the pressure foot 11 to bear against the piston 5 of the cartridge 4 causing a dose of medicament to be dispensed through an attached needle.

The distal travel of the drive member 14 is limited by the guide slots (not shown) of the internal housing 7. The drive member 14 is provided with a detent means (not shown) that is designed to interact with the pawl means (not shown) of the internal housing 7.

Audible and tactile feedback to indicate that the dose has been dispensed is provided by the interaction of the detent of the drive member 14 with the pawl means of the internal housing 7. Additionally, visual feedback regarding dose dispensing may be indicated by an optional graphical status indicator, provided on the drive member 14, which can be viewed through an optional window aperture in the main housing part 3.

Further doses may be delivered as required up to a pre-determined maximum number of doses.

Figure 2:
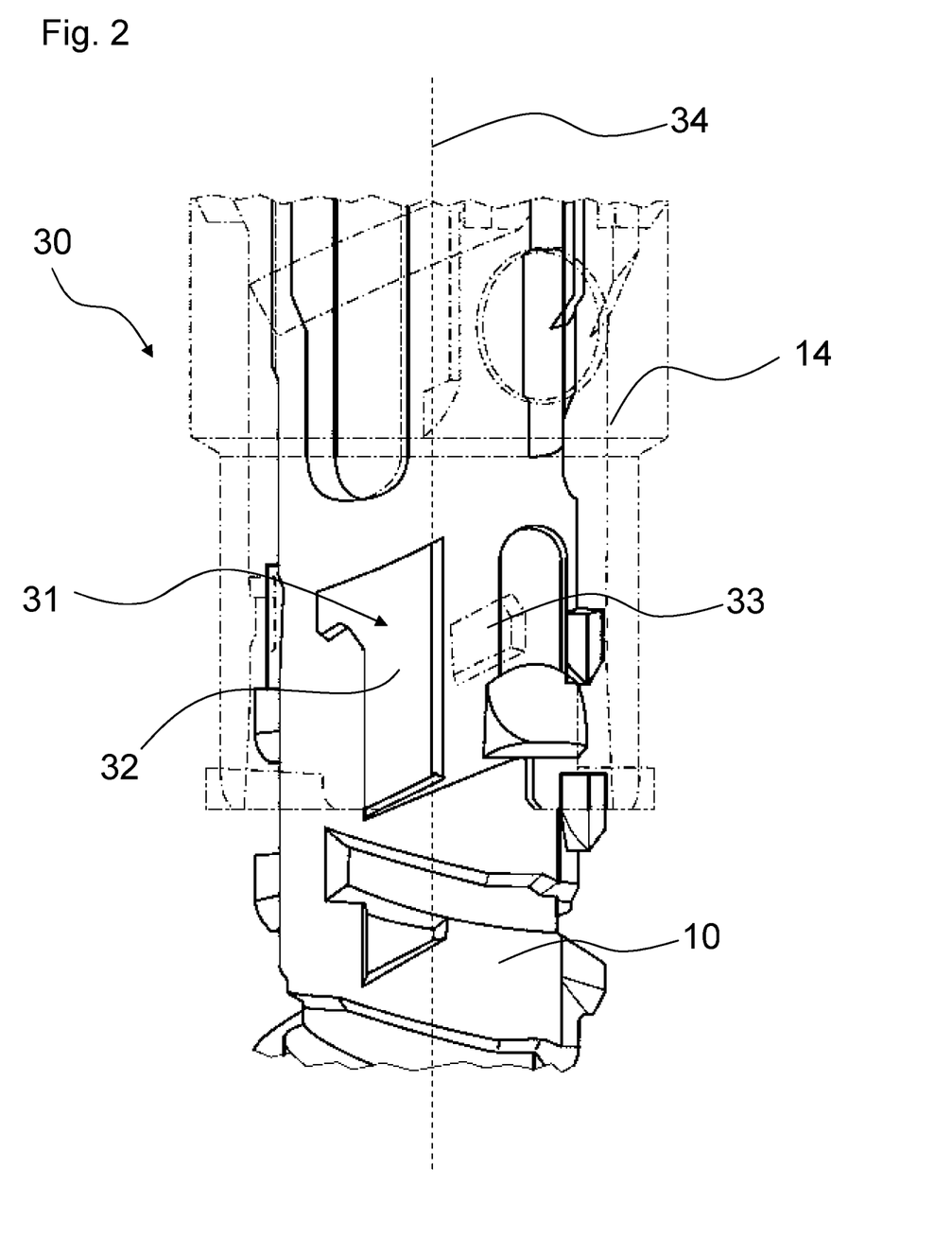
FIG. 2 shows a part of an assembly for a drug delivery device.

FIG. 2 shows a part of the assembly 30 of the drug delivery device 1 shown in FIG. 1. The assembly 30 comprises a stop mechanism 31 and the actuator 16 (not shown in FIG. 2). The shape and the arrangement of the actuator 16 are shown in FIG. 1. Furthermore, the assembly comprises the drive member 14 and the piston rod 10. The actuator 16 is arranged at the proximal end of the drive member 14, as shown in FIG. 1. In FIG. 2, the drive member 14 is illustrated with broken lines. Furthermore, the assembly may comprise the main housing part 3, which is shown in FIG. 1.

The stop mechanism 31 is configured to inhibit an actuation of the actuator 16 after the setting of a dose, when a maximum amount of a medication has been delivered from the drug delivery device 1. In particular, an actuation of the actuator 16 may be inhibited when the pre-determined maximum number of doses has been delivered. Thereby, an indication may be given to a user, that a maximum number of doses has been dispensed, and the user may recognize that the drug delivery device is empty.

After a pre-determined maximum number of doses has been delivered, a last setting movement of the actuator 16, respectively the drive member 14 is enabled. During this last setting movement, the actuator 16 and the drive member 14 are moved in a proximal direction. In particular, the drive member 14 and the actuator 16 perform an axial, non-rotational movement. During this movement, the drive member 14 is moved along the piston rod 10 in a proximal direction. The piston rod 10 is axially and rotationally fixed during the setting movement of the actuator 16. At the end of the last setting movement, the actuator 16 protrudes from the drug delivery device 1. Yet, a depression of the actuator 16 is inhibited by means of the stop mechanism 31 after the last setting movement.

The stop mechanism 31 comprises a first stop element 32 and a second stop element 33. The first stop element 32 is arranged at the piston rod 10. In particular, the first stop element 32 is fixedly attached to the piston rod 10 or is an integral part of the piston rod 10. In particular, the first stop element 32 is configured as a longitudinal protrusion on the piston rod 10, which extends along a longitudinal axis of the drug delivery device 1. For example, the piston rod 10 may be an injection moulded part, and the first stop element 32 may be integrally moulded with the piston rod 10. The second stop element 33 is arranged at the drive member 14. In particular, the second stop element 33 is fixedly attached to the drive member 14 or is an integral part of the drive member 14. In particular, the second stop element 33 is arranged at an inner surface of the drive member 14. In particular, the second stop element is configured as a protrusion on the drive member 14. For example, the drive member 14 may be an injection moulded part, and the second stop element 33 may be integrally moulded with the drive member 14.

In FIG. 2, the assembly 30 is shown in a state after a last dose of medication has been delivered. In this state, the first and the second stop element 32, 33 abut each other. In particular, during the dispense of the last dose, the drive member 14 and the piston rod 10 rotate with respect to each other, such that at the end of this rotation the first stop element 32 and the second stop element 33 abut each other. In particular, the first stop element 32 and the second stop element 33 abut each other when a maximum amount of medication has been delivered from the device, respectively when the device is empty. After a last dose of medication has been delivered, a last setting movement is still possible, since the stop mechanism 31 allows an axial movement of the drive member 14 in a proximal direction with respect to the piston rod 10. During the last setting movement, the second stop element 33, which is arranged on the drive member 14, moves axially along the first stop element 32 of the piston rod 10.

After the last setting movement, the stop mechanism 31 inhibits an actuation of the actuator 16 due to an interaction of the first stop element 32 and the second stop element 33. When a user tries to depress the actuator 16 after the last setting movement, an axial force in a distal direction is exerted on the drive member 14. This force is transmitted to the piston rod 10, and the piston rod 10 tries to perform a combined rotational and axial movement. When the piston rod 10 tries to rotate, the first stop element 32 of the piston rod is pressed against the second stop element 33 of the drive member 14. Since the drive member 14 is rotationally secured with respect to the main housing part 3 of the drug delivery device 1, a rotation of the piston rod 10 is inhibited due to the presence of the second stop element 33. Thereby, the drug delivery device is locked. In particular, a further dispensing of a dose and a further setting of a dose is inhibited.

When the device is blocked, the actuator 16 may permanently protrude from the drug delivery device 1. Thereby, a user may instantly recognize that the drug delivery device 1 is empty. In order to intensify this indication, areas of the drive member 14 or of the actuator 16 which are visible after the last setting movement may be colored. These areas are invisible for a user when the actuator 16 has been pushed into the drug delivery device 1, i. e. after the dispensing of a dose.

Figure 3:
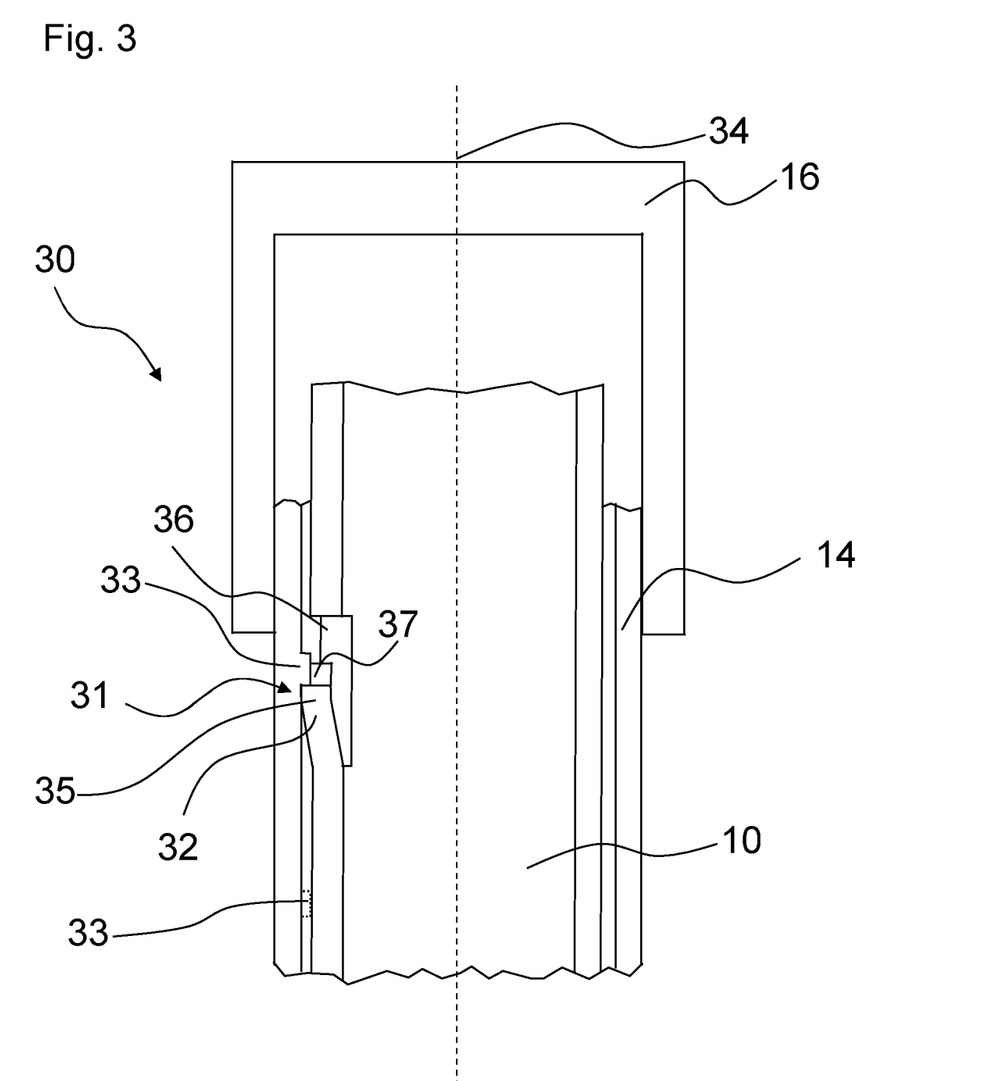
FIG. 3 shows a further embodiment of a part of an assembly for a drug delivery device.

FIG. 3 shows a sectional view of a part of an alternative assembly 30 for the drug delivery device 1 shown in FIG. 1. The assembly 30 comprises a stop mechanism 31 and the actuator 16. The stop mechanism 31 shown in FIG. 3 works similar as the stop mechanism described with reference to FIG. 2. Yet, there are some differences, which are described in the following.

The assembly 30 further comprises the drive member 14 and the piston rod 10. The actuator 16 is also arranged at the proximal end of the drive member 14. For clarity reasons, only a section of the drive member 14 and the piston rod 10 is shown. The drive member 14 and the piston rod 10 may further extend in a distal and proximal direction, which is indicated by a jagged line.

Just as the stop mechanism described with reference to FIG. 2, the stop mechanism 31 is configured to inhibit an actuation of the actuator 16 after the setting of a dose, when a maximum amount of a medication has been delivered from the drug delivery device 1. Regarding the working principle of the device during a last setting movement it is referred to the description of FIG. 2. In particular, the relative movements of the actuator 16, the drive member 14 and the piston rod 10 are the same as described in the description of FIG. 2.

In contrast to the embodiment of FIG. 2, the first stop element 32 is configured as a spring element. In particular, the first stop element 32 comprises a resilient arm 35. The first stop element 32, in particular the resilient arm 35 extends in longitudinal direction. The resilient arm protrudes from the piston rod in a radial outward direction with respect to the longitudinal axis 34 of the drug delivery device 1. During the last setting movement, the resilient arm 35 is configured to be deflected in a radial inward direction. In particular, the resilient arm 35 is deflected when the second stop element 33 moves along the resilient arm 35, in particular pushes the resilient arm 35 in a radial inward direction. When the resilient arm 35 is in an undeflected condition, it extends in a radial direction from an outer surface of the piston rod 10. In particular the resilient arm 35 extends as far as an inner surface of the drive member 14.

At the proximal end of the first stop member 32, the piston rod 10 comprises a piston rod hole 36. Due to the piston rod hole 36, the first stop element 32 may be deflected in a radial inward direction more easily. In particular, the frictional forces during a deflection of the first stop element 32 are reduced due to the piston rod hole 36.

At its proximal end, the first stop element 32 comprises a cut-out 37. The cut-out 37 is configured to receive the second stop element 32 after the last setting movement. In particular, the first stop element 32 snaps back into its undeflected position after the last setting movement. Thereby, the second stop 33 element engages with the cut-out 37.

The second stop element 33 is similar to the second stop element of FIG. 2. In particular, the second stop element 33 is configured as a protrusion on the inner surface of the drive member 14.

The position of the second stop element 33 before a last setting movement is shown by dotted lines in FIG. 3. During the last setting movement, the drive member 14, in particular the second stop element 33 is moved in a proximal direction along the piston rod 10. Thereby, the second stop element 33 is moved past the first stop element 32, in particular past the resilient arm 35. In particular, the second stop element 33 abuts the first stop element 32. Thereby, the resilient arm 35 is deflected in a radial inward direction by the presence of the second stop element 33. At the end of the last setting movement, the second stop element 33 and the cut-out 37 of the first stop element 32 are aligned with respect to each other in a radial direction. Thereby, the resilient arm 35 may relax into its undeflected position. When the resilient arm 35 relaxes into its undeflected position after a last setting movement the second stop element 33 latches into the cut-out 37 of the first stop element 32. FIG. 3 shows the assembly in a position after a last setting movement.

When the second stop element 33 is engaged with the first stop element 32, in particular with the cut-out 37, the device is locked. In particular, a relative rotation of the piston rod 10 is inhibited. When the piston rod 10 is disabled to rotate, an axial movement of the drive member 14 in a distal direction is inhibited. The actuator 16 may not be depressed. Thereby, a further dispense movement is inhibited.

The invention claimed is:

1. An assembly for a drug delivery device, the assembly comprising:
    an actuator which is configured to perform a setting movement in order to set a dose of a medication, and which is configured to perform a dispense movement in order to dispense the dose of the medication; and
    a stop mechanism which is configured to allow the setting movement of the actuator after a maximum amount of the medication has been delivered and to inhibit the dispense movement of the actuator after the setting movement when the maximum amount of the medication has been delivered,
    wherein the stop mechanism comprises a first stop element and a second stop element, and wherein the first stop element and the second stop element are configured to interact with each other to inhibit the dispense movement of the actuator,
    wherein the first stop element comprises a resilient arm which is configured to be deflected in a radial direction by the second stop element during the setting movement of the actuator after the maximum amount of the medication has been delivered, and
    wherein the second stop element is configured to be moved along the first stop element in a proximal direction during the setting movement of the actuator after the maximum amount of the medication has been delivered.

2. The assembly according to claim 1, further comprising a main housing part, wherein the dispense movement of the actuator corresponds to a depression of the actuator into the main housing part, and wherein the depression of the actuator into the main housing part is inhibited after the maximum amount of the medication has been delivered.

3. The assembly according to claim 1, wherein the first stop element and the second stop element are configured to abut each other after the maximum amount of the medication has been delivered.

4. The assembly according to claim 1, wherein the first stop element is configured to be relaxed into its undeflected position at an end of the setting movement of the actuator after the maximum amount of the medication has been delivered.

5. The assembly according to claim 1, wherein the first stop element comprises a cut-out and wherein the second stop element is configured to engage with the cut-out of the first stop element at an end of the setting movement of the actuator after the maximum amount of the medication has been delivered.

6. The assembly according to claim 1, wherein the assembly comprises a piston rod and wherein the first stop element is attached to the piston rod.

7. The assembly according to claim 6, wherein the assembly comprises a drive member which is configured to drive the piston rod, and wherein the second stop element is attached to the drive member.

8. The assembly according to claim 7, wherein the second stop element is configured as a protrusion of the drive member.

9. The assembly according to claim 7, wherein the drive member is configured to be moved in a proximal direction with respect to the piston rod during the setting movement of the actuator.

10. The assembly according to claim 7, wherein the drive member is fixedly coupled with the actuator.

11. The assembly according to claim 7, wherein the drive member is rotationally fixed with respect to a main housing part during the setting movement and during dispensing of the dose.

12. The assembly according to claim 7, wherein the drive member is configured to be moved in a distal direction during dispensing of the dose, and wherein the stop mechanism is configured to inhibit a movement of the drive member in the distal direction after a ast setting movement.

13. The assembly according to claim 6, wherein the piston rod is configured to rotate and axially move in a distal direction during dispensing of the dose.

14. A drug delivery device comprising:
    a housing;
    a cartridge retained in the housing, the cartridge containing a medication comprising at least pharmaceutically active compound;
    an actuator which is configured to perform a setting movement in order to set a dose of the medication to be dispensed from the cartridge, and which is configured to perform a dispense movement in order to dispense the dose of the medication; and a stop mechanism which is configured to allow the setting movement of the actuator after a maximum amount of the medication has been delivered and to inhibit the dispense movement of the actuator after the setting movement when the maximum amount of the medication has been delivered, wherein the stop mechanism comprises a first stop element and a second stop element, and wherein the first stop element and the second stop element are configured to interact with each other to inhibit the dispense movement of the actuator, wherein the first stop element comprises a resilient arm which is configured to be deflected in a radial direction by the second stop element during the setting movement of the actuator after the maximum amount of the medication has been delivered, and wherein the second stop element is configured to be moved along the first stop element in a proximal direction during the setting movement of the actuator after the maximum amount of the medication has been delivered.

15. A method of operating a drug delivery device, the method comprising:

setting a dose of a medication to be dispensed by moving an actuator to cause a setting movement of the actuator;

dispensing a maximum amount of the medication by moving the actuator to cause a dispense movement of the actuator; and, after dispensing the maximum amount of the medication, moving the actuator to cause the setting movement of the actuator and to cause a first stop element to abut a second stop element, thereby inhibiting the dispense movement of the actuator, wherein the first stop element comprises a resilient arm which is configured to be deflected in a radial direction by the second stop element during the setting movement of the actuator after the maximum amount of the medication has been delivered.

16. The method of claim 15, wherein:

moving the actuator to cause the setting movement of the actuator comprises pulling the actuator in a proximal direction relative to a main housing part, and moving the actuator to cause the dispense movement of the actuator comprises depressing the actuator in a distal direction relative to the main housing part.

17. The method of claim 15, wherein moving the actuator to cause the setting movement of the actuator after dispensing the maximum amount of the medication comprises moving the actuator such that a first stop element abuts a second stop element.

* * * * *

UNITED STATES PATENT AND TRADEMARK OFFICE
CERTIFICATE OF CORRECTION

PATENT NO. : 10,357,613 B2
APPLICATION NO. : 14/914760
DATED : July 23, 2019
INVENTOR(S) : Michael Jugl and Axel Teucher Page 1 of 1

It is certified that error appears in the above-identified patent and that said Letters Patent is hereby corrected as shown below:

In the Claims

Column 14, Line 56, Claim 12, delete "ast" and insert -- last --.

Signed and Sealed this
Twenty-fourth Day of December, 2019

Andrei Iancu
*Director of the United States Patent and Trademark Office*